United States Patent
Loo et al.

(10) Patent No.: US 9,616,031 B2
(45) Date of Patent: Apr. 11, 2017

(54) METHOD FOR ENCAPSULATING PARTICLES

(75) Inventors: Say Chye Joachim Loo, Singapore (SG); Yit Lung Khung, Singapore (SG); Wei Li Lee, Singapore (SG)

(73) Assignee: Nanyang Technological University, Singapore (SG)

( * ) Notice: Subject to any disclaimer, the term of this patent is extended or adjusted under 35 U.S.C. 154(b) by 718 days.

(21) Appl. No.: 13/885,820

(22) PCT Filed: Nov. 24, 2011

(86) PCT No.: PCT/SG2011/000413
§ 371 (c)(1),
(2), (4) Date: Jul. 17, 2013

(87) PCT Pub. No.: WO2012/071013
PCT Pub. Date: May 31, 2012

(65) Prior Publication Data
US 2013/0302429 A1    Nov. 14, 2013

Related U.S. Application Data

(60) Provisional application No. 61/416,989, filed on Nov. 24, 2010, provisional application No. 61/465,569, filed on Mar. 21, 2011.

(51) Int. Cl.
*A61K 9/50* (2006.01)
*A61K 9/51* (2006.01)
(Continued)

(52) U.S. Cl.
CPC .......... *A61K 9/5089* (2013.01); *A61K 9/5031* (2013.01); *B01J 13/02* (2013.01);
(Continued)

(58) Field of Classification Search
None
See application file for complete search history.

(56) References Cited

U.S. PATENT DOCUMENTS 4,230,685 A * 10/1980 Senyei ................... A61K 35/12
                                                            210/222
6,153,266 A    11/2000 Yokogawa et al.
(Continued)

FOREIGN PATENT DOCUMENTS

| WO | WO 00/00177 | 1/2000 |
| WO | WO 2008/149096 | 12/2008 |
| WO | WO 2010/036919 | 4/2010 |

OTHER PUBLICATIONS

J DeRuiter. "Amides and Related Functional Groups." Principles of Drug Action 1, Spring 2005, Amides. http://www.auburn.edu/~deruija/pda1_amides.pdf, accessed Jan. 7, 2016. pp. 1-16.*
(Continued)

*Primary Examiner* — Isaac Shomer
(74) *Attorney, Agent, or Firm* — Schiff Hardin LLP (57) ABSTRACT

The present invention relates to a method for encapsulating particles of a water-insoluble material within a capsule of a water-insoluble polymer, comprising (a) dispersing particles of the water-insoluble material or a solution containing the water-insoluble material in a first aqueous phase containing a first surfactant to obtain a first dispersion; (b) collecting the particles of the water-insoluble material coated with the first surfactant; (c) washing the collected particles; (d) adding the washed surfactant-coated water-insoluble material particles to a polymer solution containing the water-insoluble polymer of the capsule to obtain a polymer mixture; and (e) dispersing the polymer mixture in a second aqueous phase containing a second surfactant to obtain a second dispersion
(Continued)

comprising the particles of the water-insoluble material encapsulated within the capsule of the water-insoluble polymer.

22 Claims, 9 Drawing Sheets

(51) Int. Cl.
*B01J 13/02* (2006.01)
*C09B 67/08* (2006.01)
*A61K 9/16* (2006.01)

(52) U.S. Cl.
CPC ........ *C09B 67/0013* (2013.01); *A61K 9/1647* (2013.01); *A61K 9/5084* (2013.01); *A61K 9/5153* (2013.01)

(56) References Cited

U.S. PATENT DOCUMENTS

| | | | |
|---|---|---|---|
| 2002/0141957 A1* | 10/2002 | Tan | A61K 8/26 424/63 |
| 2008/0095822 A1* | 4/2008 | Maquet | A61K 9/0019 424/426 |
| 2008/0248122 A1* | 10/2008 | Rashba-Step | A61K 9/1647 424/490 |
| 2010/0172999 A1* | 7/2010 | Marteaux | A45C 11/00 424/490 |

OTHER PUBLICATIONS

Y Lin, L Wang, P Zhang, X Wang, X Chen, X Jing, Z Su. "Surface modification of poly(L-lactic acid) to improve its cytocompatibility via assembly of polyelectrolytes and gelatin." Acta Biomateriala, vol. 2, 2006, pp. 155-164.*

S Mallakpour, F Zeraatpisheh. "Pseudo-poly(amino acid)s: study on construction and characterization of novel chiral and thermally stable nanostructured poly(ester-imide)s containing different trimellitylimido-amino acid-based diacids and pyromellitoyl-tyrosine-based diol." Colloid Polymer Sci, vol. 289, 2011, pp. 1055-1064.*

Taguchi, T., et al., "Apatite coating on hydrophilic polymer-grafted poly(ethylene) films using an alternate soaking process" Biomaterials, vol. 22 pp. 53-58 (2001).

Yanagida, H., et al., "Cell adhesion and tissue response to hydroxyapatite nanocrystal-coatet poly(L-lactic acid) fabric", Journal of Bioscience and Bioengineering vol. 108, No. 3, pp. 235-243 (2009).

Jongpaiboonkit, L., et al., "Growth of Hydroxyapatite Coatings on Biodegradable Polymer Microspheres", Applied Materials & Interfaces, vol. 1, No. 7, pp. 1504-1511 (2009).

Zhang, R., et al., "Porous poly(L-lactic acid)/apatite composites created by biomimetic process", Journal of Biomedical Materials Research, vol. 45, Issue 4, pp. 285-293 (1999).

Kang, S.W., et al., "Apatite-coated poly(lactic-co-glycolic) microspheres as an injectable scaffold for bone tissue engineering", Journal of Biomedical Materials Research, vol. 85A (3), pp. 747-756 (2007).

Virto, M.R., et al., "Improvement of gentamicin poly(D,L-lactic-co-glycolic acid) microspheres for treatment of osteomyelitis induced by orthopedic procedures", Biomaterials, vol. 28, pp. 877-885 (2007).

Choi, S.-W., et al., "Design of surface-modified poly(D,L-lactide-co-glycolide) nanoparticles for targeted drug delivery to bone", Journal of Controlled Release, vol. 122, pp. 24-30 (2007).

Di Silvio, L., et al., "Biodegradable drug delivery system for the treatment of bone infection and repair", Journal of Material Science: Materials in Medicine, vol. 10, pp. 653-658 (1999).

Xu, Q., et al., "Controlled release of amoxicillin from hydroxyapatite-coated poly(lactic-co-glycolic acid) microspheres", Journal of Controlled Release, vol. 127, pp. 146-153 (2008).

Mallakpour et al., "Pseudo-poly(amino acid)s: study on construction and characterization of novel chiral and thermally stable nanostructured poly(ester-imide)s containing different trimellitylimido-amino acid-based diacids and pyromellitol-tyrosine-based diol", Colloid and Polymer Science, 2011, vol. 289, pp. 1055-1064.

* cited by examiner

METHOD FOR ENCAPSULATING PARTICLES

CROSS-REFERENCE TO RELATED APPLICATION

This application claims the benefit of priority of U.S. Provisional Patent Application No. 61/416,989, filed 24 Nov. 2010, and U.S. Provisional Patent Application No. 61/465,569, filed 21 Mar. 2011, the contents of which being hereby incorporated by reference in their entirety for all purposes.

TECHNICAL FIELD

The invention relates to a method of encapsulating particles, and in particular, to a method of encapsulating particles of a water-insoluble material within a capsule of a water-insoluble polymer.

BACKGROUND

Drug delivery is the administration of a pharmaceutical agent to achieve a therapeutic effect in patients receiving the pharmaceutical agent. Conventional drug delivery strategies often require repetitive drug administrations and this can lead to strong fluctuating drug levels that may pose undue physiological discomfort to the patient. Furthermore, certain drugs at high concentrations can sometimes trigger undesirable toxicity or immunological responses in the patient, which may sometimes be detrimental.

As such, proper drug administration requires a fine balance between time, dosage, mode of delivery and more importantly, should aid in improving patient compliance and clinical outcomes. These factors consequently lead to the emergence of biodegradable polymer-based drug delivery carriers or vehicles, due to their ability to degrade to harmless by-products while providing desirable drug release profiles. In fact, designing these polymer-based delivery carriers or vehicles has been one of the focal points in numerous drug delivery studies in recent years.

Drug release profiles are usually altered through the direct tailoring of the chemistry or structural composition of the polymeric matrix. Subsequently, the release of the drugs is achieved either by diffusion through the polymer matrix, gradual dissolution of the polymer, by catalytic action from enzymes in-vivo or a combination of these. A great deal of work had been done in engineering a variety of different particle types, encompassing various shapes, sizes, morphologies, and in evaluating how these can affect drug release kinetics.

While the conventional approach in the literature largely revolved around designing of polymeric platforms for the administration of a single drug formulation, basic economics and patient compliance are factors that would favor the realization of a single carrier that can host and release multiple drug entities. Ideally, such carriers should be able to simultaneously entrap and release multiple drugs in a controlled manner, which would eliminate the need for repeated administrations. However, attaining such a carrier platform presents a major challenge in the field of drug delivery due to certain physicochemical considerations.

SUMMARY

The present invention provides a single carrier that can host and release multiple drug entities.

According to one aspect of the invention, there is provided a method for encapsulating particles of a water-insoluble material within a capsule of a water-insoluble polymer. The method includes:

(a) dispersing particles of the water-insoluble material or a solution containing the water-insoluble material in a first aqueous phase containing a first surfactant to obtain a first dispersion;

(b) collecting the particles of the water-insoluble material coated with the first surfactant;

(c) washing the collected particles;

(d) adding the washed surfactant-coated water-insoluble material particles to a polymer solution containing the water-insoluble polymer of the capsule to obtain a polymer mixture; and (e) dispersing the polymer mixture in a second aqueous phase containing a second surfactant to obtain a second dispersion comprising the particles of the water-insoluble material encapsulated within the capsule of the water-insoluble polymer.

According to another aspect of the invention, there is provided a capsule formed of a water-insoluble polymer, including particles of a water-insoluble material encapsulated therein. The capsule may be useful in drug delivery or bioimaging applications.

BRIEF DESCRIPTION OF THE DRAWINGS

In the drawings, like reference characters generally refer to the same parts throughout the different views. The drawings are not necessarily drawn to scale, emphasis instead generally being placed upon illustrating the principles of various embodiments. In the following description, various embodiments of the invention are described with reference to the following drawings.

DESCRIPTION

The following detailed description refers to the accompanying drawings that show, by way of illustration, specific details and embodiments in which the invention may be practised. These embodiments are described in sufficient detail to enable those skilled in the art to practise the invention. Other embodiments may be utilized and changes may be made without departing from the scope of the invention. The various embodiments are not necessarily mutually exclusive, as some embodiments can be combined with one or more other embodiments to form new embodiments.

The present invention provides for a multi-drug delivery system, whereby a solid/water/oil/water (S/W/O/W) emulsion technique is modified to obtain a polymeric capsule having multiple different drug-loaded particles encapsulated therein.

By employing the present method, sub-micron sized particles (microparticles) hosting a variety of different chemical agents, dyes or drugs can be concurrently loaded into a single hollow larger microcapsule. The approach to achieve this would be firstly, to fabricate different chemically-loaded (micro-)particles in separate batches before encapsulating them together in a larger microcapsule. The microparticles can be concomitantly loaded with one or more different drugs before finally being packaged into a single microcapsule. Furthermore, such a system could reduce any burst release phenomena often associated with particulate systems, as the shell of microcapsule can act as a barrier against rapid drug losses. Lastly, the shell of the microcapsule can act as a membrane for drug diffusion to achieve drug release in a highly controlled manner.

In various embodiments, a method for encapsulating particles of a water-insoluble material within a capsule of a water-insoluble polymer is provided. The method includes:

(a) dispersing particles of the water-insoluble material or a solution containing the water-insoluble material in a first aqueous phase containing a first surfactant to obtain a first dispersion;

(b) collecting the particles of the water-insoluble material coated with the first surfactant;

(c) washing the collected particles;

(d) adding the surfactant-coated water-insoluble material particles to a polymer solution containing the water-insoluble polymer of the capsule to obtain a polymer mixture; and (e) dispersing the polymer mixture in a second aqueous phase containing a second surfactant to obtain a second dispersion comprising the particles of the water-insoluble material encapsulated within the capsule of the water-insoluble polymer.

As mentioned above, the present method refers to a modified emulsion technique. Emulsification refers to the process of emulsifying in which two immiscible liquids are mixed together (e.g. by shaking, stirring or homogenizing) forming an emulsion. Thus, an emulsion is a disperse system of two or more immiscible liquids. One of the liquids forms a dispersant (also called continuous phase) in which the other phase (also called dispersed phase) is distributed in form of fine droplets. Emulsifying of one liquid in the other results in the formation of small droplets of one liquid dispersed (separated and distributed throughout the space) in the other liquid.

Most emulsions consist of water and oil as immiscible phases. Depending on the composition and ratio of the phases two distribution options exist. In case water "W" is the continuous phase and the oil "O" is the dispersed phase, the result is an "O/W emulsion" whose basic character is determined by the aqueous phase. If oil "O" is the continuous phase and water "W" the dispersed phase, the result is a "W/O emulsion", whose basic character is determined by the oil.

When applying this knowledge to the method of the present invention, it becomes obvious that the method of the present invention uses a S/W/O/W emulsion for the manufacture of capsules of the present invention as will be illustrated with reference to FIG. 1.

Figure 1:
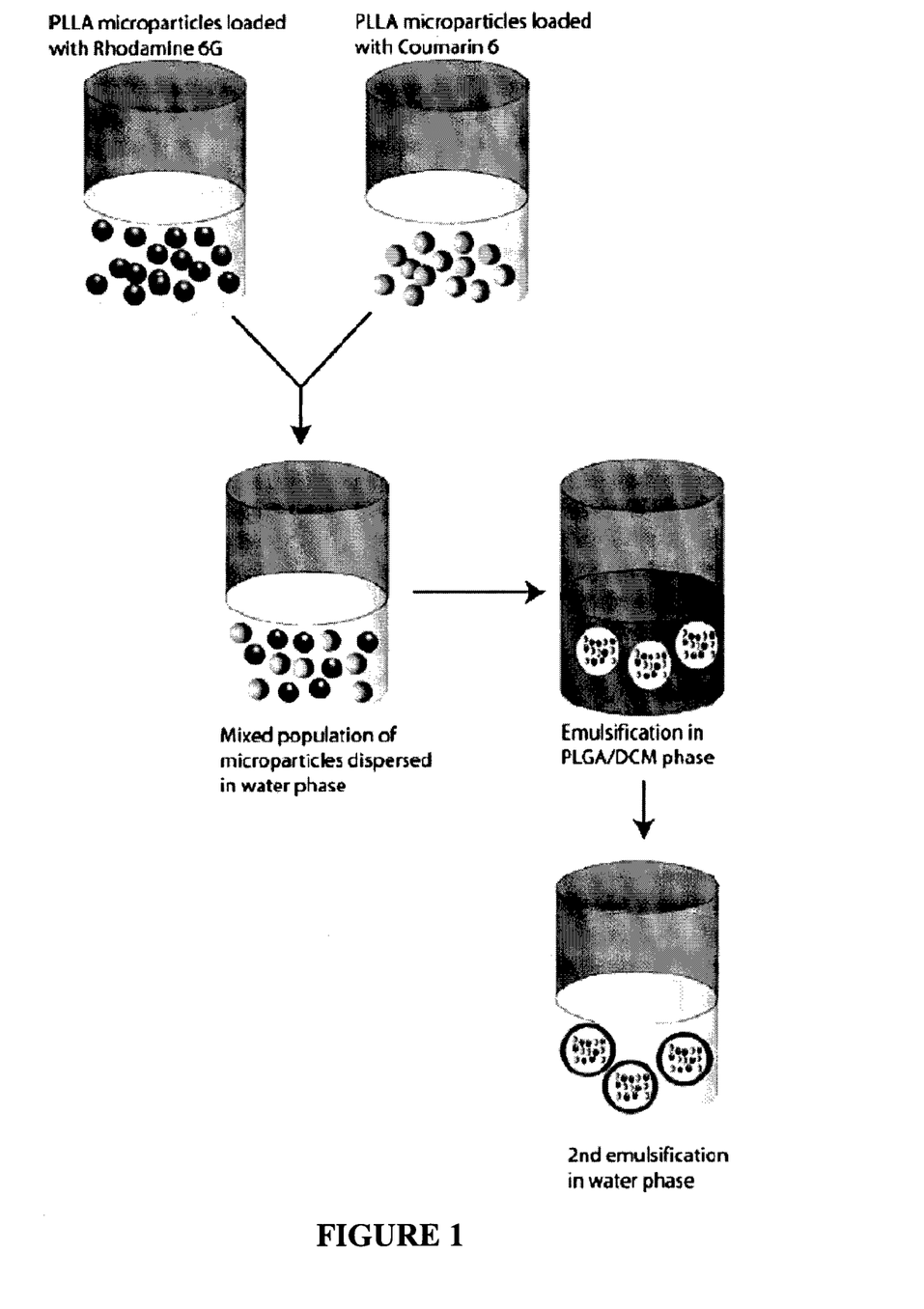
FIG. 1 shows an illustration of simultaneous encapsulation of particles loaded with two different dyes within a single capsule.

FIG. 1 shows an illustration of simultaneous encapsulation of particles loaded with two different dyes within a single capsule. At first, two solutions are provided. The first solution is an organic solvent in which particles of a water-insoluble material (in this illustration, a polymer) has been dispersed. The second solution is an organic solvent in which particles of a further water-insoluble material (in this illustration, also a polymer) has been dispersed. It is to be understood and appreciated that while the water-insoluble material and the further water-insoluble material illustrated in this embodiment are polymers, other types of particles, for example, metal oxide nanoparticles such as iron oxide nanoparticles or titanium dioxide nanoparticles, are also possible. For convenience and illustration purposes only, particles to be encapsulated consisting of polymer(s) are described in subsequent paragraphs. The particles in both solutions may be the same or different. The particles may further comprise a marker substance and/or therapeutic agent, depending on the target applications in which the resultant capsules of the present invention will be used.

In the embodiment illustrated in FIG. 1, the particles of the water-insoluble material consist of poly(L-lactic acid) (PLLA) microparticles. The PLLA microparticles are loaded with Rhodamine 6G (i.e. a dye). The particles of the further water-insoluble material consist of PLLA microparticles. The PLLA microparticles are loaded with Coumarin 6 (i.e. a dye). The first and second surfactants used are polyvinyl alcohol (PVA). The polymer solution containing the water-insoluble polymer consists of a poly(D,L-lactic-co-glycolic acid)/dichloromethane (PLGA/DCM) phase.

The two solutions containing the two different dye-loaded microparticles are then dispersed in a first aqueous phase to obtain a first dispersion ("S/W" emulsion). The microparticles may be dispersed by sonication and/or agitation such as stirring. The aqueous phase may be water or phosphate-buffered saline (PBS) solution, for example. The first aqueous phase further comprises a first surfactant for stabilizing the microparticles in the S/W emulsion during subsequent emulsification. The maintenance of the surfactant on the microparticles surface is crucial for subsequent emulsification. For this purpose, another volume of the first aqueous phase containing the first surfactant may be added to the S/W emulsion to ensure sufficient surfactant is coated onto the microparticles surfaces. The surfactant-coated microparticles are then collected. Examples of collecting the surfactant-coated microparticles include, but are not limited to, centrifuging, filtering or sieving the dispersion to separate the surfactant-coated microparticles from the aqueous phase.

The collected surfactant-coated microparticles are then washed by a washing agent. Examples of a washing agent include, but are not limited to, de-ionized water, distilled water, or isopropyl alcohol. In one embodiment, the collected surfactant-coated microparticles are rinsed with de-ionized water before being added to a polymer solution containing the water-insoluble polymer of the capsule. The aqueous suspension containing the microparticles may be added dropwise to the polymer solution. The polymer mixture thus obtained forms the S/W/O emulsion of the present system.

To stabilize the microparticles in the final S/W/O/W emulsion, the microparticles are emulsified in a second aqueous phase containing a second surfactant to form the capsule. The microparticles are emulsified by dispersing the polymer mixture in the second aqueous phase. The dispersing may be carried out by sonication and/or agitation such as stirring for example. The aqueous phase may be water or phosphate-buffered saline (PBS) solution, for example. The surfactant positions itself at the interface between the capsule formed and the second aqueous solution comprising the surfactant. This final S/W/O/W emulsion is then allowed to evaporate the solvents to obtain the capsules, which may be centrifuged and washed before lyophilizing and storing them.

Examples of organic solvents for dissolving the polymeric particles used in the method of the present invention include ethyl acetate (EAc), acetone, methyl ethyl ketone (MEK), tetrahydrofuran (THF), chloroform, pentane, benzene, benzyl alcohol, propylene carbonate (PC), carbon tetrachloride, methylene chloride (dichloromethane or DCM) or acetonitrile. As mentioned above, in one example of the present invention DCM is used as organic solvent for both the first solution and the second solution.

The organic solvent used for the first solution and the second solution may be the same or different. Organic solvents which are volatile at room temperature or which have a low boiling point are preferred, i.e. in most of the cases a boiling point equal or below 70° C.

The polymers used in the method of the present invention can be biodegradable or non-biodegradable polymers. Biodegradable polymers are synthetic or natural polymers which degrade in vivo either enzymatically/non-enzymatically to produce biocompatible or non-toxic by-products along with the progressive release of the encapsulated hydrophilic, hydrophobic and amphiphilic active compound.

Examples of polymers which can be used in the method of the present invention can include, but are not limited to a polyester, a polyanhydride, a polyorthoester, a polyphosphazene, a pseudopolyamino acid, a natural polymer, a polyamide, a polystyrene, ethylene vinyl acetate, polybutadiene, a polyurea, (poly) acrylate, a methacrylate, an acrylatemethacrylate copolymer, polyarylsulfone (PAS), a polyurethane, a polyalkylcyanocarylate, a polyphosphazene or copolymers and/or combinations thereof.

Further examples include, polyethylene, fluorinated polyethylene, poly-4-methylpentene, polyacrylonitrile, a polyamide-imide, polybenzoxazole, polycarbonate, polycyanoarylether, polyestercarbonate, polyether, polyetheretherketone, polyetherimide, polyetherketone, polyetherimide, polyetherketone, polyethersulfone, polyfluoroolefin, a polyimide, a polyolefin, polyoxadiazole, polyphenylene oxide, polyphenylene sulfide, polypropylene, a polysulfide, a polysulphone, polytetrafluoroethylene, a polythioether, a polytriazole, a polyvinyl, polyvinylfluoride, a silicone, urea-formaldehyde or copolymers or mixtures of these polymers.

In one example, a copolymer composed of a polyanhydride, such as Poly[bis(p-carboxy-phenoxy)propane anhydride] (CPP), polymerized with sebacic acid (SA or decanedioic acid) can also be used as polymer in the method of the present invention, wherein the ratio of CPP to SA can vary. For example, combinations, such as pCPP:SA or 20:80, 50:50 can be used. Instead of SA, it is also possible to use dodecanedioic acid (DD). Further examples for other polyanhydrides include, but are not limited to poly(malic anhydride), poly (adipic anhydride) or poly (sebacic anhydride).

Non-limiting examples for a natural polymer can include, but are not limited to a protein or a polysaccharide, wherein a protein can be, e.g., albumin, globulin, gelatin, fibrinogen, collagen or casein. Examples for suitable polysaccharides can include, but are not limited to starch, cellulose, such as cellulose ether and cellulose ester, chitosan, dextran, alginic acid, inulin or hyaluronic acid.

Non-limiting examples for polyesters can include, but are not limited to poly($\epsilon$-caprolactone) (PCL), poly(lactic acid) (PLA or PLLA), poly(glycolic acid) (PGA), polyesteramide (PEA), Poly(hydroxylbutyrate-co-hydroxyvalerate (PHB or PHBV; polyhydroxyalkanoate), an aliphatic copolyester, such as poly(butylene succinate adipate) (PBSA), an aromatic copolyester, such as poly(butylene adipate-co-terephthalate) (PBAT), and poly(lactic-co-glycolic acid) (PLGA).

Aromatic copolyesters, such as poly(butylene adipate-co-terephthalate) (PBAT) are often based on terephtalic diacid while aliphatic copolyesters are obtained by the combination of diols such as: 1,2-ethanediol, 1,3-propanediol or 1,4-butadenediol, and dicarboxylic acid: adipic, sebacic or succinic acid. The biodegradability of aliphatic copolyester depends partly on their structure. The addition of adipic acid, which decreases the cristallinity tends to increase the biodegradation. The addition of starch filler can significantly improve the rate of degradation of an aliphatic copolyester.

For example, PLGA comprises of successive monomeric units (of glycolic or lactic acid) which are linked together in PLGA by ester linkages, thus yielding a linear, aliphatic polyester as a product. Depending on the ratio of lactide to glycolide used for the polymerization, different forms of PLGA can be obtained: these are usually identified in regard to the monomers' ratio used (e.g. PLGA 75:25 identifies a copolymer whose composition is 75% lactic acid and 25% glycolic acid. All PLGAs are amorphous rather than crystalline. PLGA degrades by hydrolysis of its ester linkages in the presence of water. The time required for degradation of a PLGA is related to the monomers' ratio used in production: the higher the content of glycolide units, the lower the time required for degradation. An exception to this rule is the copolymer with 50:50 monomers' ratio which exhibits the faster degradation (about two months). In addition, polymers that are end-capped with esters (as opposed to the free carboxylic acid) demonstrate longer degradation half-lives. Thus, the present invention also refers to PLGAs or other polymers which are chemically modificated, such as the modified PLGA mentioned above comprising end-capped esters. Furthermore, the present invention also refers to PLGAs or other polymers which have an —OH or acidic end group. Polymers modified to comprising an —OH or acidic end group degrade even faster than end-capped polymers. Polymer comprising —OH or acidic end groups are commercially available.

Polymers, such as PCL, PGA, PLA and PLGA are of interest in the biomedical area because of their biocompatibility and biodegradability properties. In particular, PLGA has been FDA approved for human therapy. When degrading, PLA and PLGA chains are cleaved in the body to monomeric acids, i.e. lactic and glycolic acids that are eliminated from the organism through Kreb's cycle as $CO_2$ and in urine as water.

Examples for PLGA that can be used in the method of the present invention include, but are not limited to PLGA 50:50 (lactide/glycolide molar ratio), PLGA 55:45, PLGA 85:15, PLGA 75:25, PLGA 53:47 or PLGA 80/20. However, other ratios are also possible and are also suitable to be used in the method of the present invention.

In various embodiments, the polymer of the water-insoluble material, the polymer of the further water-insoluble material and the polymer of the water-insoluble polymer are different.

In various embodiments, the polymer of the water-insoluble polymer has a faster degradation rate than the polymer of the water-insoluble material and the further water-insoluble material.

In one embodiment, the water-insoluble material consists of PLLA and the water-insoluble polymer consists of PLGA.

The surfactant used to stabilize the particles and/or capsules in the respective emulsions can include, but is not limited to, an amphoteric surfactant, an anionic surfactant, a cationic surfactant, a nonionic surfactant or mixtures thereof. Depending on the polymers used, the surfactant can influence the size of the microparticles formed.

Examples of an anionic surfactant can include, but are not limited to sodium dodecyl sulfate (SDS), sodium pentane sulfonate, dehydrocholic acid, glycolithocholic acid ethyl ester, ammonium lauryl sulfate and other alkyl sulfate salts, sodium laureth sulfate, alkyl benzene sulfonate, soaps, fatty acid salts or mixtures thereof.

Examples of a nonionic surfactant can include, but are not limited to poloaxamers, alkyl poly(ethylene oxide), diethylene glycol monohexyl ether, polyvinyl alcohol (PVA), copolymers of poly(ethylene oxide) and poly(propylene oxide), hexaethylene glycol monohexadecyl ether, alkyl polyglucosides, digitonin, ethylene glycol monodecyl ether, cocamide MEA, cocamide DEA, cocamide TEA, fatty alcohols or mixtures thereof. In one example, PVA has been used to stabilize the microparticles in the emulsion.

Poloaxamers, such as F127, are difunctional block copolymer surfactants terminating in primary hydroxyl groups. They are composed of a central hydrophobic chain of polyoxypropylene (poly(propylene oxide)) flanked by two hydrophilic chains of polyoxyethylene (poly(ethylene oxide)). Because the lengths of the polymer blocks can be customized, many different poloxamers exist having slightly different properties. For the generic term "poloxamer", these copolymers are commonly named with the letter "P" (for poloxamer) followed by three digits, the first two digits×100 give the approximate molecular mass of the polyoxypropylene core, and the last digit×10 gives the percentage polyoxyethylene content (e.g., P407=Poloxamer with a polyoxypropylene molecular mass of 4,000 g/mol and a 70% polyoxyethylene content). For the Pluronic tradename, coding of these copolymers starts with a letter to define it's physical form at room temperature (L=liquid, P=paste, F=flake (solid)) followed by two or three digits, the first digit(s) refer to the molecular mass of the polyoxypropylene core (determined from BASF's Pluronic grid) and the last digit×10 gives the percentage polyoxyethylene content (e.g., F127=Pluronic with a polyoxypropylene molecular mass of 4,000 g/mol and a 70% polyoxyethylene content). In one example, poloxamer 407 (P407) (=Pluronic F127) or F-188 or L-63 or mixtures thereof can be used.

Examples of a cationic surfactant can include, but are not limited to cetyl trimethylammonium bromide (CTAB), dodecylethyldimethylammonium bromide (D12EDMAB), didodecyl ammonium bromide (DMAB), cetylpyridinium chloride (CPC), polyethoxylated tallow amine (POEA), hexadecyltrimethylammonium p-toluenesulfonate, benzalkonium chloride (BAC), benzethonium chloride (BZT) and mixtures thereof.

Examples of an amphoteric surfactant can include, but are not limited to dodecyl betaine, sodium 2,3-dimercaptopropanesulfonate monohydrate, dodecyl dimethylamine oxide, cocamidopropyl betaine, 3-[N,N-dimethyl(3-palmitoylaminopropyl)ammonio]-propanesulfonate, coco ampho glycinate and mixtures thereof.

As previously mentioned, particles of the water-insoluble material can include, for example, a marker substance such as a dye or a therapeutic agent such as a drug, for example a small molecule drug, a peptide, a protein or a nucleic acid.

Examples of dyes or fluorophores include, but are not limited to Coumarin-6, Rhodamine 6G, Fluorescein, Umbelliferone, Styryl, Hexacyanin, Dibenzocyanin, Phenoxazon, Pinacyanol, Kryptocyanin, Pyrromethene, Exalite, Quinolon, Stilben, Uranin, Sulforhodamin, and mixtures thereof.

Hydrophilic drugs or pharmaceuticals which can be encapsulated can comprise all kinds of pharmaceuticals. The capsules can comprise, for example, pharmaceuticals effective for the prevention or treatment of the gastrointestinal tract/metabolism; blood and blood forming organs; cardiovascular system; skin; reproductive system; endocrine system; infections and infestations; malignant disease; immune disease; muscles, bones, and joints; brain and nervous system; respiratory system or mixtures thereof. The capsules can also comprise antidotes, contrast media, radiopharmaceuticals and dressings or mixtures thereof.

Examples of some common pharmaceuticals/drugs include, but are not limited to, ibuprofen, metoclopramide, atorvastatin, clopidogrel, enoxaparin, celecoxib, omeprazole, esomeprazole, fexofenadine, quetiapine, metoprolol and budesonide.

Encapuslation of vaccines, such as group B *Streptococcus* vaccine (GBS), tetanus toxoid (TT), Japanese encephalitis virus (JEV), diphtheria toxoid (DT), *vibrio cholerae* (VC), SPF 66 malaria vaccine, multivalent vaccines of *Haemophilus influenza* type b (Hib), pertussis toxin (PT), Rotavirus to name only a few, is also possible.

Examples of proteins which can be encapsulated include bovine serum albumin (BSA), recombinant human epidermal growth factor (rhEGF), recombinant human erythropoietin (rhEPO), protein-C, ribozymes, vapreotide (somastatin analogue), orntide acetate (LHRH antagonist), growth factors, such as insulin like growth factor-1 (IGF-1), vascular endothelial growth factor (VEGF); ovalbumin, human chorionic gonadotropin (hCG), human serum albumin (HSA), recombinant human morphogenetic protein-2 (rhBMP) and calcitonin, to name only a few examples.

Figure 6:
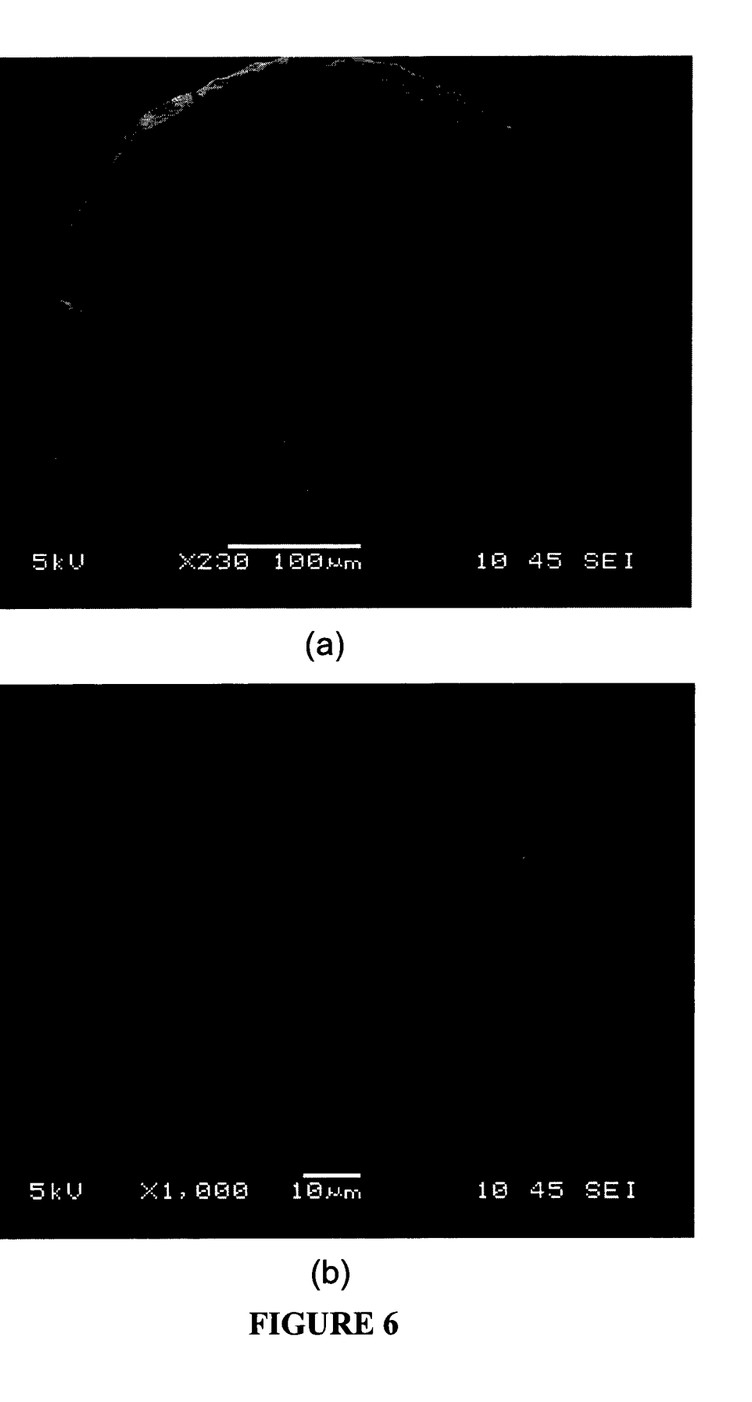
FIG. 6 shows SEM images of a PLGA capsule (with porous structure) encapsulating PLLA particles. (a) Cross-sectional view of a whole capsule and (b) close-up view.

As an example, FIG. 6 shows SEM images of a PLGA capsule (with porous structure) encapsulating PLLA particles ((a) Cross-sectional view of a whole capsule and (b)

close-up view). By carefully manipulating the process parameters in the fabrication, the PLGA capsules with porous structure can be produced, in which the PLLA particles were found to reside within each small cavity. The multi-compartment within the capsule was achieved by reducing the volume of aqueous suspension containing the PLLA particles or increasing the polymer precipitation rate at the encapsulation stage. The precipitation rate can be increased by increasing the polymer solution concentration, stirring speed, temperature, and air flow, for example.

The polymer candidates for both the particles and the capsule shell are selected on the basis of their intrinsic rate of degradation in aqueous conditions. Typically, the outer shell of the capsule would consist of a polymer that will degrade relatively quickly while the particles would have a much slower degradation rate.

The stirring speed for forming both the particles and the capsule determines the size of the capsule as well as the density by which the number of particles were packed within the capsules.

Manipulation of the molecular weight and the amount of the polymer used for the capsule is pivotal to the drug release profile of the particles.

By selecting different oil phase, it will be possible to change both the size of the particles as well as the overall dispersion of the capsule. It will also allow for the fine tuning of the particle packing density.

The present invention represents a huge advancement in the fields of simultaneous multiple drugs delivery platform. By the means of tailoring the encapsulating candidate, it is now possible to use this invention to fine tune both the drug type as well the selection for an appropriate and desirable drug release profile. For example, a single microcapsule having a size of 100 microns can holds up to 1.2 million nanoparticles and this in principle also equate being able to encapsulate 1.2 million drugs and therapeutics in a single compartment if each single nanoparticle is 100 nm in diameter. While this is not logistically feasible, it does demonstrate the potential of the present carrier system in the field of drug delivery. For example, diseases such as HIV and Lupus are often in need for multiple drug administration and these particles will certainly be able to help in improving the prognosis of these disease.

Another possible application is to use this delivery system for pulmonary delivery. The key problem in the current technology in pulmonary delivery is that the size of the carriers has to be 1-5 µm to achieve deep lung delivery. Any larger or smaller would not achieve this. At the same time, the delivery of nanoparticles is essential in pulmonary treatment because cells need to take up these small particles for better therapeutic efficacy. With the present method, nanoparticles can be delivered into the deep lung region through the use of microparticles. The nanoparticles are encapsulated within a biodegradable microparticle with the intended purpose of pulmonary delivery.

The pulmonary delivery system was developed based on two key design considerations: 1) Sub-micron sized particles (1-5 µm) that allow for deep lung delivery and 2) Subsequent release of encapsulated nanoparticles into the deep lung provides controlled drug release, and stimulate uptake by specific targeted cells (e.g. alveolar macrophages). Together, both these factors are essential to enhance pulmonary delivery and treatment. Here, the encapsulated nanoparticles could be drug-loaded nanoparticles (i.e. protein, drugs, peptides, antibodies etc. for therapy) and/or nanoparticles for bioimaging (diagnostic) or for biosensing. This could be used for targeting tuberculosis, an infectious pulmonary disease. For therapeutic applications (eg. to treat pulmonary diseases, asthma, pneumonia, edema, cancer, etc.), the route of delivery could be via pulmonary, intraveneous, subcutaneous, intramascular, for example.

Non-biomedical applications may also be possible i.e. any application that requires a larger particle to encapsulate a smaller particle.

In order that the invention may be readily understood and put into practical effect, particular embodiments will now be described by way of the following non-limiting examples.

EXAMPLES

Materials

PLLA (intrinsic viscosity (IV): 2.38, Bio Invigor), PLGA (50:50) (IV: 1.18, Bio Invigor) and poly(vinyl alcohol) (PVA) (molecular weight: 30-70 kDa, Sigma-Aldrich) were used without further purification. MCA, IBU, laser grade Coumarin-6 (C6) and Rhodamine 6G (R6G) fluorescent dyes were purchased from Sigma-Aldrich. Dichloromethane (DCM) was from Tedia Co., Inc. Phosphate-buffered saline (PBS) solution (pH 7.4) was purchased from OHME, Singapore. All chemicals and solvents were used as received.

Fabrication of PLLA Nanoparticles

PLLA nanoparticles were first formed by dissolving 0.3 g of PLLA (6% w/v) in 5 ml of DCM and this polymeric solution was stirred overnight. Subsequently the solution was added to 10 ml of de-ionized water with 6% of PVA (w/v). The mixture was then subjected to an ultrasound probe for sonication for 3 h before quickly being transferred to 240 ml of PVA/de-ionized water at 2% w/v. Subsequently, the nanoparticles were stirred at 2000 rpm for 3 hours and left overnight in the fumehood for solvent evaporation. The nanoparticles were then collected by centrifugation and rinsed once with de-ionized water. The supernatant was carefully decanted and the nanoparticles were reconstituted in 10 ml of water.

Encapsulation of PLLA Nanoparticles in PLGA Microcapsule

Figure 7:
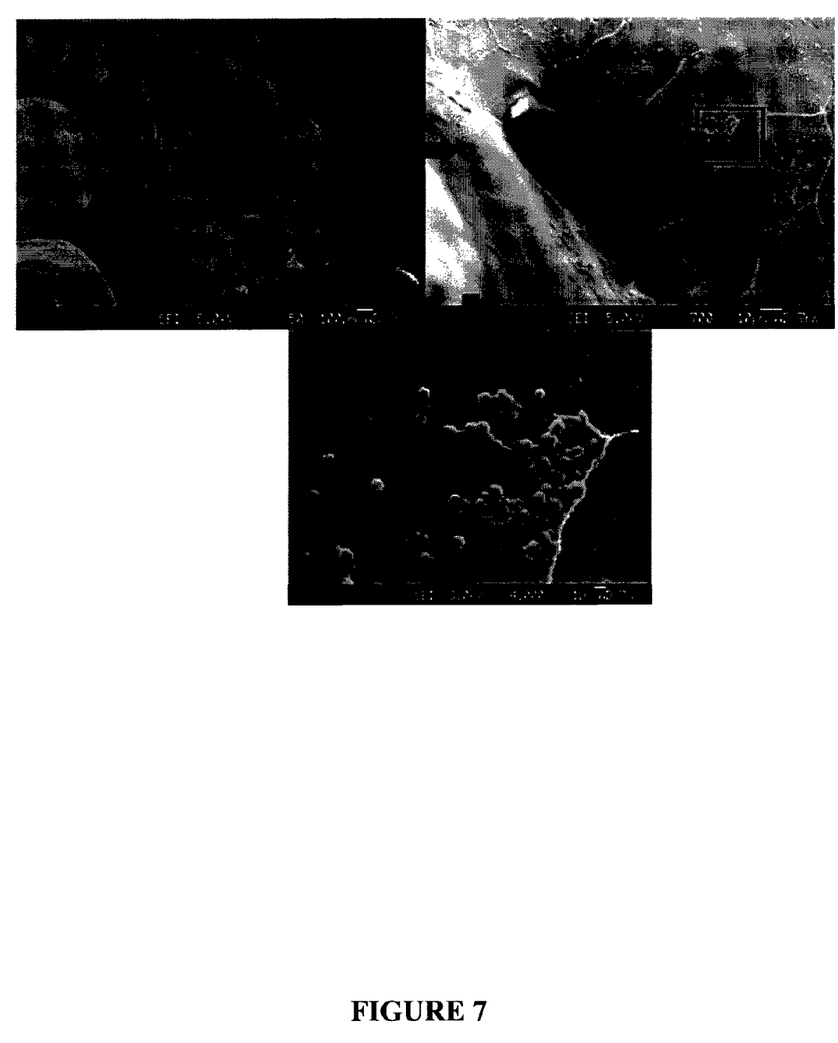
FIG. 7 shows FESEM of a PLGA microcapsule with PLLA nanoparticles encapsulated within the interspatial regions.
Figure 8:
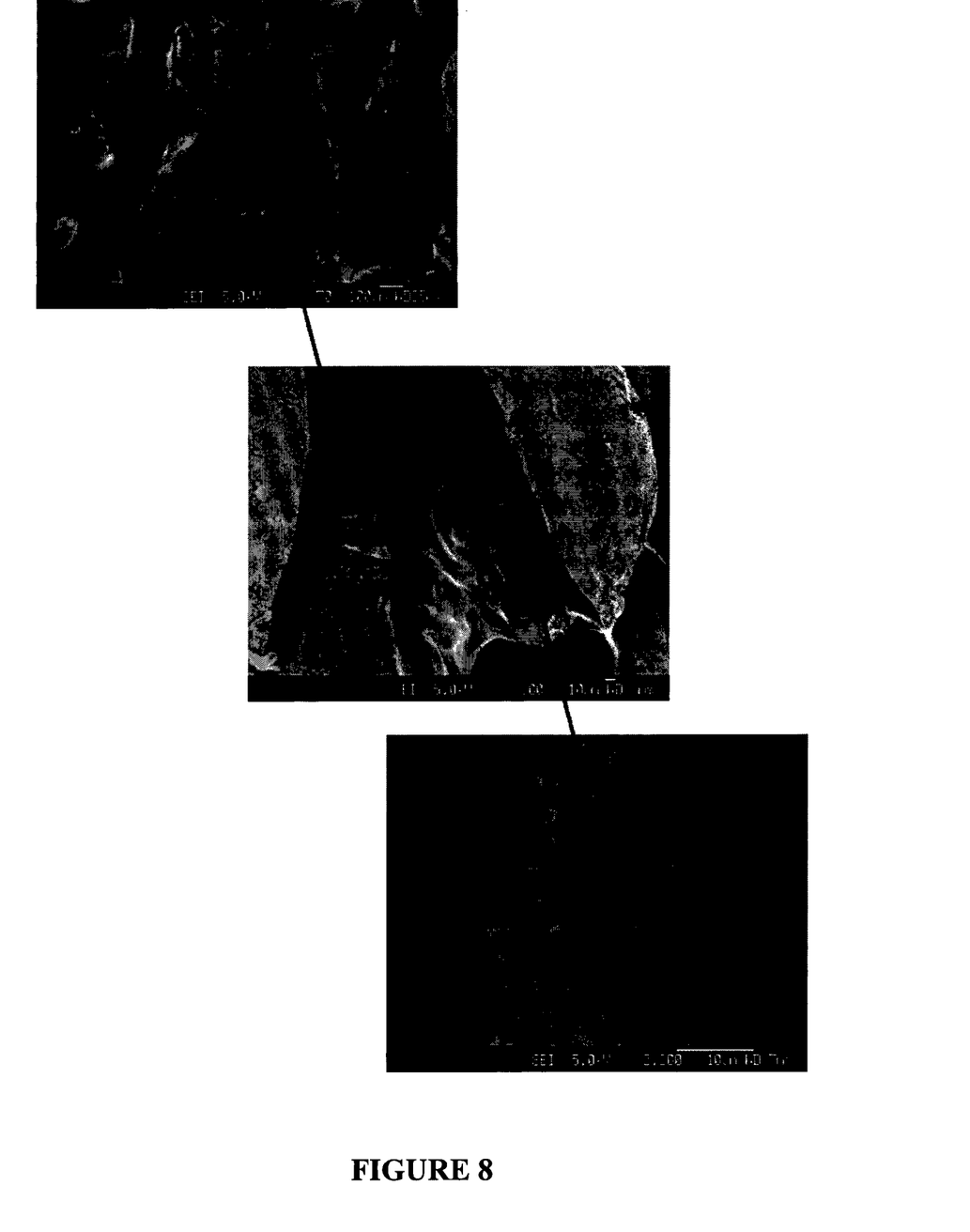
FIG. 8 shows (A) fabricated PLGA microcapsule with an average size of ~250 microns. The onsets, (B) and (C), represent subsequent higher magnification into regions within the microcapsule to reveal the presence of PLLA nanoparticles (~500-800 nm) clusters.

For the encapsulation step, 0.5 g of PLGA (16.67% w/v) was first dissolved in 3 ml of DCM. After complete dissolution, 2 ml of the reconstituted nanoparticles were introduced dropwise into the PLGA solution and flip mixed several times. After mixing, the solution was added into 250 ml of PVA solution (0.5% w/v) and was stirred at 350 rpm for 3 hours to form the microcapsule. The microcapsules were subsequently rinsed with copious amount of de-ionized water and lyophilized. FIG. 7 shows an FESEM micrograph of a cross sectional view of a typical microcapsule where the onsets represents the respective magnified regions within the same particle. FIG. 8 shows (A) fabricated PLGA microcapsule with an average size of ~250 microns. The onsets, (B) and (C), represent subsequent higher magnification into regions within the microcapsule to reveal the presence of nanoparticles (~500-800 nm) clusters.

Fabrication of Fluorophore-Loaded PLLA Microparticles

C6- and R6G-loaded PLLA microparticles were fabricated separately in two individual processes, using the conventional oil/water (O/W) emulsion solvent evaporation method.

Briefly, a homogenous polymer/dye solution (polymer: 6% (w/v); dye: 0.1% (w/v)) was prepared in which PLLA (0.3 g) in DCM (4 mL) and dye (0.005 g) in DCM (1 mL) was dissolved separately. The polymer and individual dye solution were then mixed, and the resultant polymer/dye solution was added into 10 mL aqueous solution containing PVA at 6% (w/v) as surfactant and ultra-sonicated for 1 min to form the first oil-in-water emulsion. The primary emulsion was subsequently added to 240 mL aqueous solution containing PVA at 2% (w/v) and the volatile DCM solvent was removed via overhead stirring at 1500 rpm at room temperature for 3 h. The maintenance of the PVA surfactant on PLLA microparticles surface was deemed crucial for the next emulsion packaging step and usual washing of the particles was intentionally omitted prior to encapsulation. The fluorophore-loaded PLLA microparticles were then collected by centrifuging at 10,000 rpm for 20 min.

Encapsulation of Fluorophore-Loaded Microparticles in PLGA Microcapsule

To form the microcapsule, C6-loaded particles (0.1 g) and R6G-loaded particles (0.1 g) were first added into de-ionized water (2 mL) and mixed homogenously by vortex mixer and ultra-sonication. The resultant aqueous suspension was added dropwise into a PLGA polymer solution (0.5 g of PLGA, 8% (w/v)) and the mixture was then allowed to homogenize by magnetic bar stirring at 1000 rpm for 3 min. This polymer mixture was added to 250 mL aqueous solution containing PVA at 0.5% (w/v) and emulsified at 400 rpm using an overhead stirrer at room temperature for 3 h. Finally, the microcapsules were rinsed with de-ionized water, lyophilized, and stored in desiccators for further characterization.

Drug Release from Drug-Loaded PLGA Microcapsule

In conjunction with the fluorophore studies, the validity of our model as a drug carrier was also verified using IBU- and MCA-loaded PLLA microparticles and encapsulated within a hollow PLGA microsphere following the same methodological approach as described earlier.

For control, microparticles that were loaded with the respective drug were directly used without encapsulation so as to obtain a direct comparison between the drug release profiles.

Drug-loaded microparticles (20 mg) and microcapsules (20 mg) were placed, in triplicate, in vials containing 30 mL phosphate-buffered saline (PBS) solution and were incubated at 37° C. in a shaking incubator. The PBS release medium (1 mL) was removed from each vial and analyzed using a Shimadzu UV-2501 UV-Vis spectrophotometer ($\lambda$MCA=309 nm, $\lambda$IBU=220 nm) at pre-determined time points, before being replaced with fresh PBS solution.

Characterization Techniques

Scanning Electron Microscopy (SEM)

The morphologies of microcapsules were analyzed using a JOEL (JSM-6340F) field emission scanning electron microscope (FESEM) at 5 kV. Before analysis, the samples were mounted onto metal stubs and cross-sectioned approximately at the center line with a razor blade.

Samples were then coated with platinum using a sputter coater model SPI-Module. Particle size analysis was conducted using the ImageJ software from the SEM images.

Confocal Laser Scanning Microscopy (CLSM)

Particles were placed on glass slide and covered with glass cover slip. The images were captured with Leica SP5 Confocal Microscope, using an oil immersion 40× objective lens.

The image was captured by emission wavelength of 480-600 nm bands; beam splitter: RT 70/30, pinhole 68 µm, and scanning speed of 400 Hz.

Statistical Analysis

Drug release data were evaluated by unpaired Student's t-test. Differences were considered statistically significant when P≤0.05.

Results and Discussion

Microencapsulation of Dye-Loaded Particles

Figure 2:
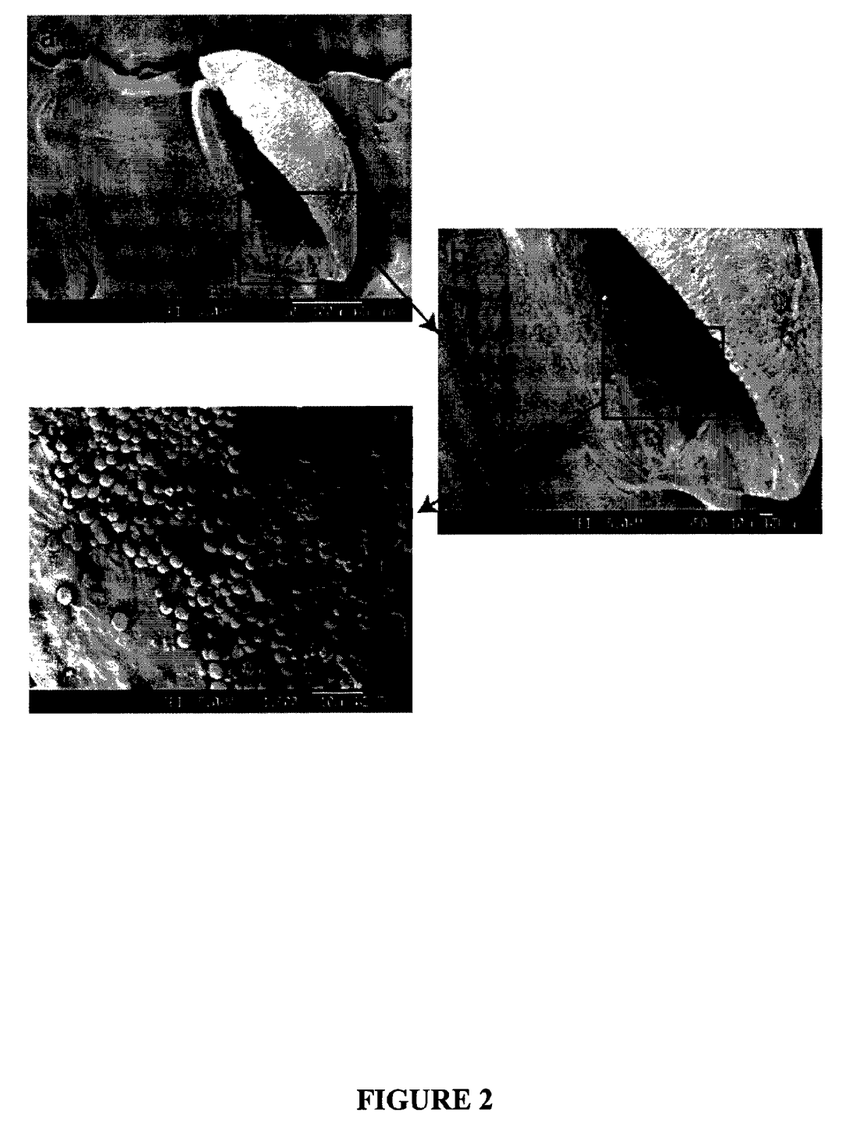
FIG. 2 shows field emission scanning electron microscopy (FESEM) images of a typical microcapsule excised to disclose the cross-section region. (a-c) Subsequent magnification had revealed the presences of smaller PLLA microparticles residing within the hollow space of the microcapsule. No microparticles were found on the outer shell region of the microcapsule.

Dye-loaded PLGA microcapsules were first fabricated and characterized to evaluate the feasibility of the concept. Initial analysis with the FESEM revealed that the typical microcapsule size obtained were approximately 250±80 µm (FIG. 2). Careful excision with a scalpel across these PLGA microcapsules had helped exposed the interior structure, thus confirming their hollow structures. Closer examination revealed many smaller microparticles (1.26 µm±0.61) on the interior walls of the PLGA microcapsules, confirming the possibility of encapsulating microparticles within a larger microcapsule. It is important to note that no microparticles were found residing on the exterior walls of the PLGA microcapsule. As both PLLA and PLGA are soluble in DCM, it was deemed necessary to maintain a high concentration of PVA surfactant on the surface of the microparticles as this was hypothesized to help impede the possibility of PLLA particles dissolving into the PLGA-DCM phase during the second emulsion step. The retention of the PVA surfactant on the PLLA microparticles was therefore deemed an important feature for achieving the desired configuration of the present carrier system.

Figure 9:
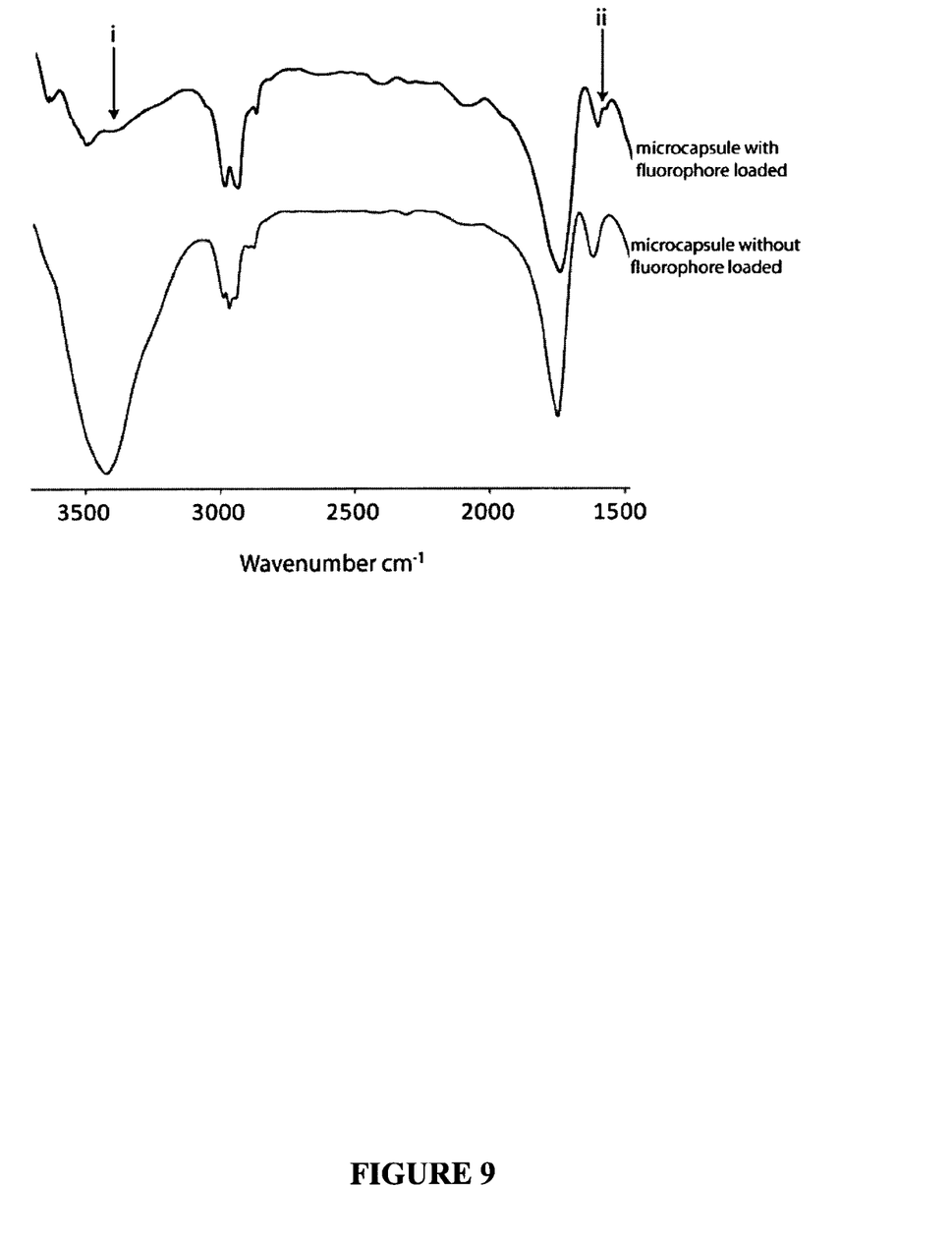
FIG. 9 shows FTIR spectra of microcapsule with the two fluorophores loaded microparticles as compared to those without any fluorophore loading. Arrows at the positions of i and ii denotes the stretching vibrations indicative for the presence of the fluorophores.

To verify the presence of the respective fluorophores, Fourier transform Infrared spectroscopy (FTIR) was performed on the microcapsules encapsulating microparticles hosting the two different fluorophores (FIG. 9). As the overall microcapsule had several different components with much similarity in chemical constitution, it would not be realistic to expect a clear discernment between them. This was especially so between PLLA and PLGA where the chemical structure is fairly similar. As shown in FIG. 9, for the microcapsules carrying microparticles with fluorophores, a weak shouldering at 3400-3500 $cm^{-1}$ (labelled i) was observed and this shouldering was not noted in the microcapsule without fluorophores. This shouldering peak had been attributed to the N—H stretching modes from either R6G or C6. Similarly, in the same spectra, another shouldering peak was also resolved (labelled ii) at the position of 1591 $cm^{-1}$ and this is the typical signature arising from the C=C stretching vibrations in aromatic systems. As both PLGA and PLLA do not contain any aromatic rings and amines, the emergence of both peaks can only be attributed from either the C6 or R6G fluorophores. These observations had confirmed the presences of the fluorophores within the microcapsules.

Figure 3:
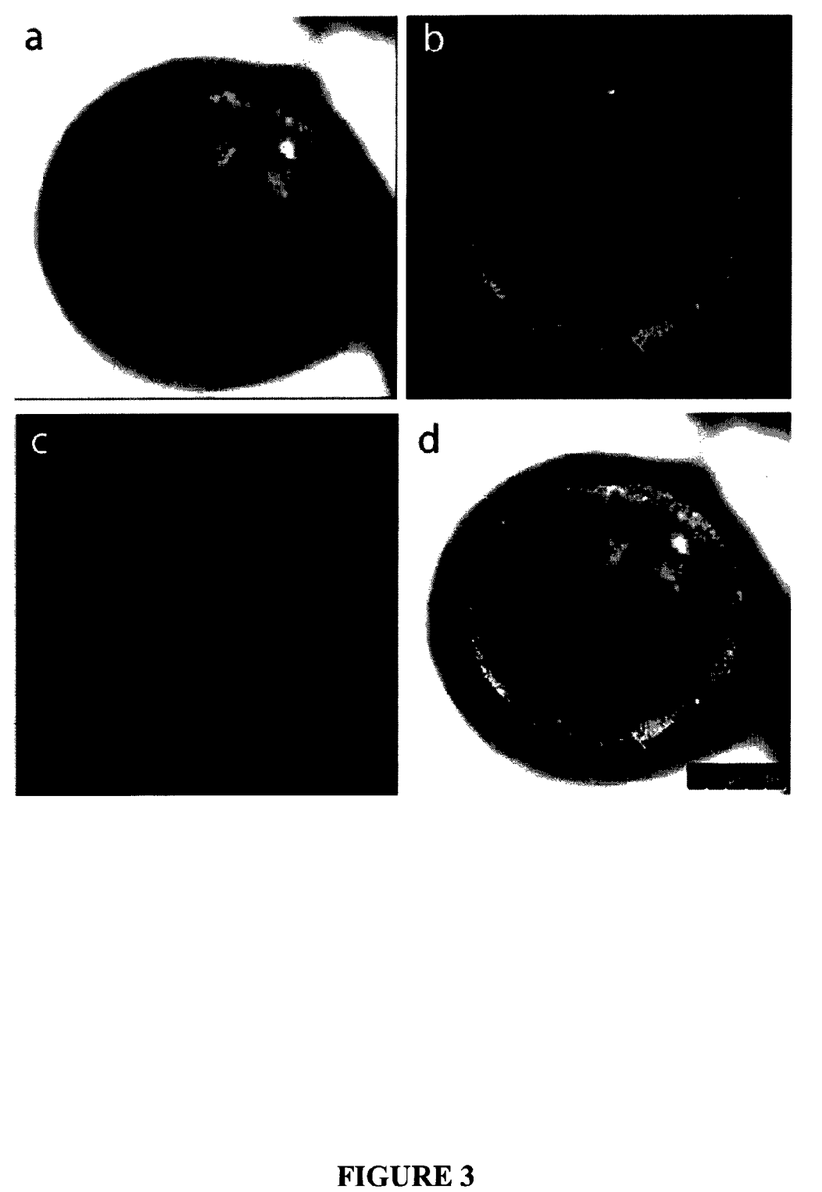
FIG. 3 shows CLSM images of a cross-sectional plane of one microcapsule. (a) Brightfield, (b) emission of the C6 dye, (c) emission of the R6G dye and (d) an overlaid representation of all the components.

In-depth fluorescent imaging with CLSM gave the strongest indications of the effectiveness of this encapsulation method. To attain a clearer visual discernment of the dyes within the microcapsule, micron-sized PLLA particles were deliberately selected as dye carriers so as to optimize their respectively fluorescence output. FIG. 3 shows the CLSM images of the PLGA microcapsule with the encapsulation of dye-loaded microparticles. As shown in FIG. 3d, the microcapsule had shown simultaneous emission spectra (520 nm for C6 and 588 nm for RG6 respectively), thus confirming the successful encapsulation of the dye-loaded microparticles within a single microcapsule. As the microcapsules were hollow, it was also possible to resolve the outline of the particle (FIG. 3a) via bright-field imaging, and the thickness of the microcapsule shell was found to be relatively homogenous (~15 µm) throughout the entire particle, which was agreeable to our SEM analysis. In conjunction, when overlaid against the two fluorophore optical images (FIGS. 3b and 3c), the fluorescence from the two components did not exceed beyond the periphery of the PLGA inner walls. In summary, this technique was proven to be effective in preparing PLGA microcapsules that can be loaded with two different fluorophore-loaded PLLA microparticles.

Drug Release Study

Figure 4:
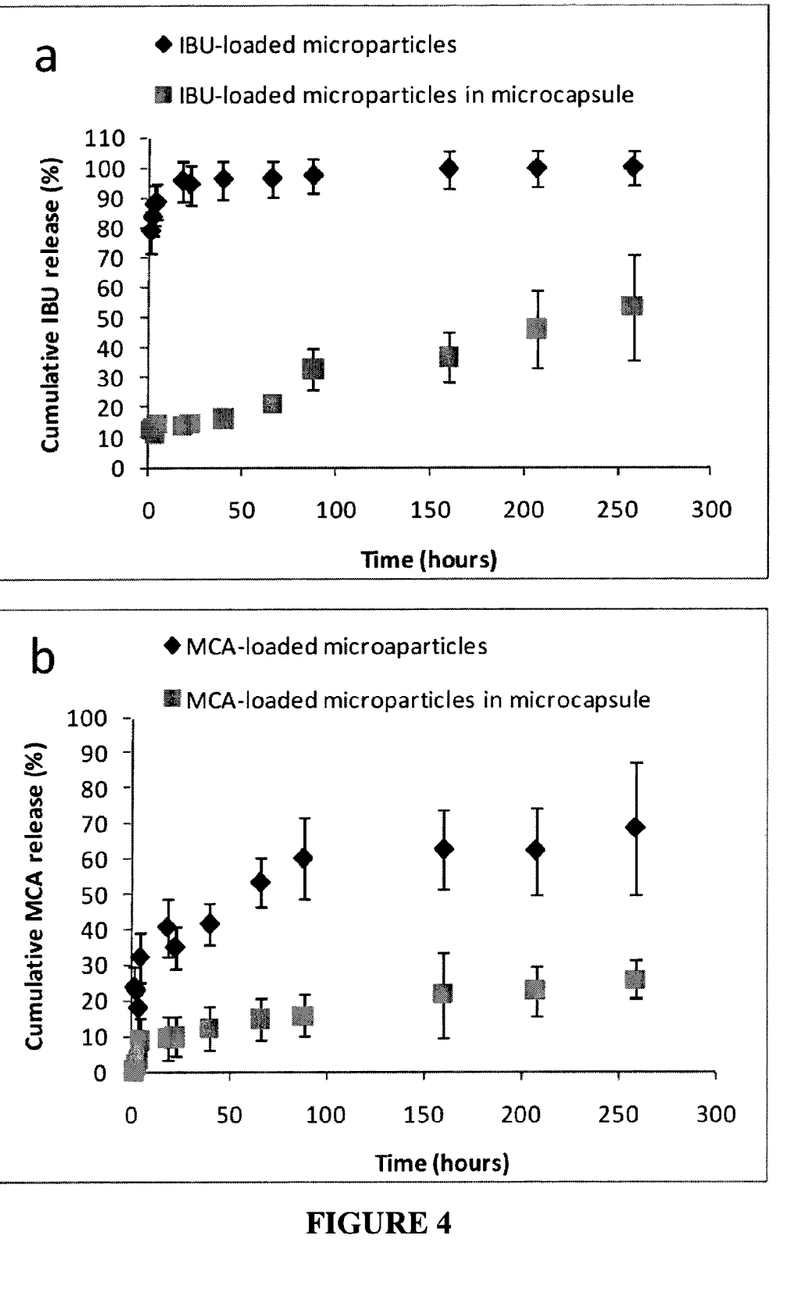
FIG. 4 shows the cumulative release profile of (a) IBU-loaded microparticles and encapsulated microparticles and (b) MCA-loaded microparticles and encapsulated microparticles. It is important to note that in (a) and (b), release profiles for the encapsulated microparticles in microcapsule had been derived from microcapsules that hosted both types of drug-loaded microparticles at the same time. Single-layered PLLA microparticles exhibited a rapid release for both hydrophilic (MCA) and hydrophobic (IBU) drugs. More interestingly, the presence of a shell in the PLGA capsules provided additional barriers to drug diffusion, effectively retarding the rapid release of drug and releasing two drugs simultaneously in a more controlled manner.
Figure 5:
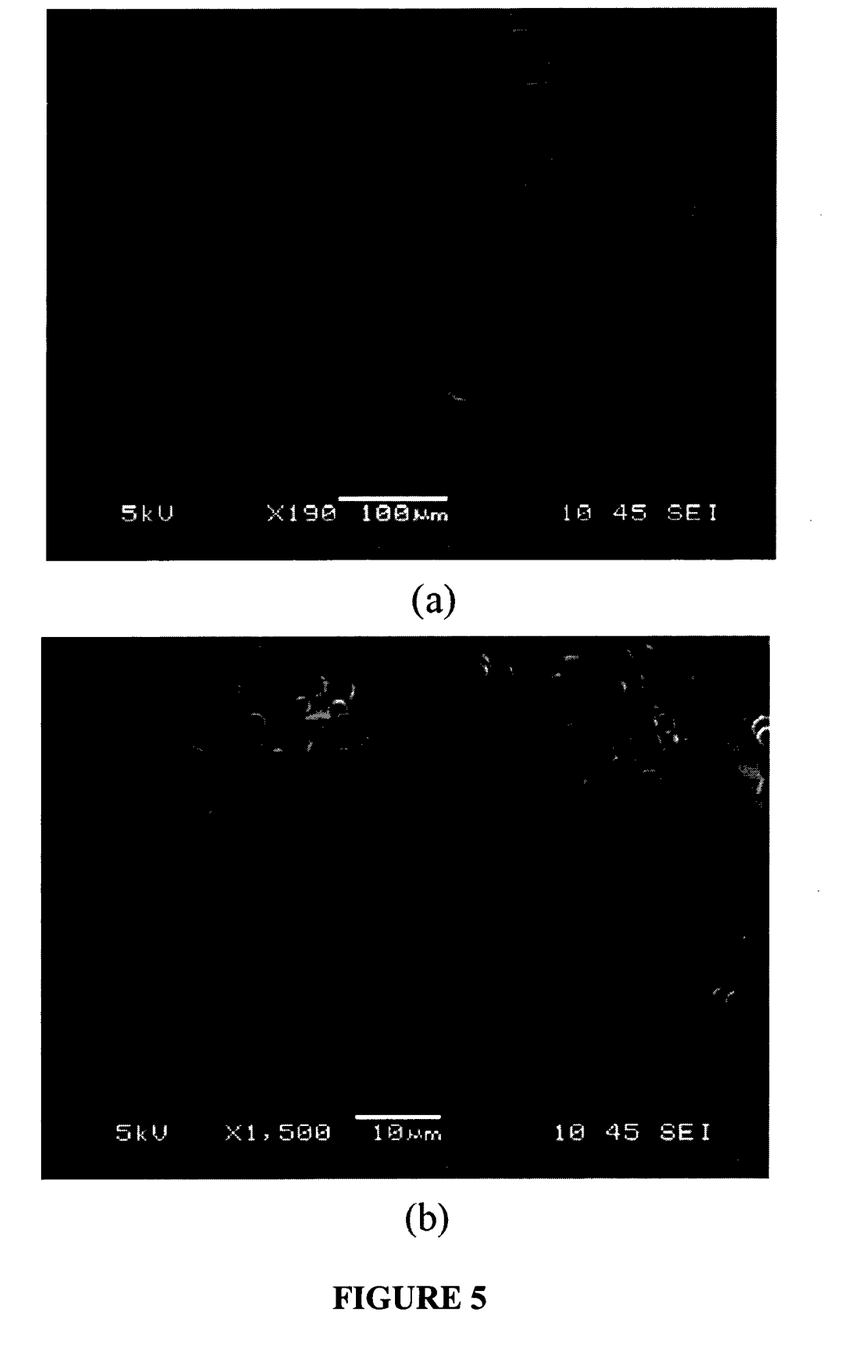
FIG. 5 shows SEM images of a capsule encapsulating particles loaded with two different drugs (i.e. IBU and MCA). (a) Cross-sectional view of a whole capsule and (b) close-up view.

Drug-loaded microparticles, in place of dyes, were subsequently used to prepare drug-loaded PLGA microcapsules. SEM images show similar results whereby the microparticles were found attached onto the inner wall of the PLGA microcapsule (FIG. 5). FIGS. 4a and 4b show the release profiles of hydrophobic IBU and hydrophilic MCA, respectively, from PLLA microparticles alone and PLGA microcapsules (i.e. encapsulated with drug-loaded PLLA microparticles). From the release studies, PLLA microparticles without encapsulation exhibited a relatively rapid release for both hydrophilic (MCA) and hydrophobic (IBU) drugs, while PLGA microcapsules had a more controlled release profile. The retardation of initial burst release was highly evident for IBU, whereby almost all the IBU drug was released from the microparticles within less than one day (95% for microparticles vs 20% for microcapsules). For the initial release of MCA from the microcapsules, the retardation was observed to be of a lesser extent (40% for microparticles vs 15% for microcapsules). While the PLLA microparticles allowed for quick influx of water and thus a faster release profile, the PLGA shell of the microcapsules limits the rate of water influx, and this effect together with the PLGA "membrane", would influence drug diffusion rates. These factors would therefore play an important role in controlling drug release profiles from PLGA microcapsules. In summary, this novel delivery system shows the ability to reduce burst release, while providing a controlled release of both hydrophilic and hydrophobic drugs over a sustained period.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numerical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

The invention claimed is:

1. A method for encapsulating particles of a water-insoluble material within a capsule of a water-insoluble polymer, comprising:
    (a) dispersing particles of the water-insoluble material or a solution containing the water-insoluble material in a first aqueous phase containing a first surfactant to obtain a first dispersion, wherein the water-insoluble material comprises or consists of at least one polymer;
    (b) collecting the particles of the water-insoluble material coated with the first surfactant;
    (c) washing the collected particles;
    (d) adding an aqueous suspension containing the washed surfactant-coated water-insoluble material particles to a polymer solution containing the water-insoluble polymer of the capsule to obtain a polymer mixture; and
    (e) dispersing the polymer mixture in a second aqueous phase containing a second surfactant to obtain a second dispersion comprising the particles of the water-insoluble material encapsulated within the capsule of the water-insoluble polymer, wherein the polymer of the water-insoluble material and the water-insoluble polymer are different, and wherein the water-insoluble polymer has a faster degradation rate than the polymer of the water-insoluble material.

2. The method of claim 1, wherein the particles of the water-insoluble material or the solution of the water-insoluble material as used in step (a) further comprises a marker substance and/or therapeutic agent.

3. The method of claim 2, wherein the solution of the water-insoluble material comprising the marker substance and/or therapeutic agent is formed by:
    dissolving the water-insoluble material in a first volume of a solvent and combining the solution with a second volume of a solvent containing the marker substance and/or therapeutic agent.

4. The method of claim 1, wherein particles of the water-insoluble material further comprise particles of a further water-insoluble material.

5. The method of claim 4, wherein the further water-insoluble material comprises or consists of at least one polymer.

6. The method of claim 4, wherein the further water-insoluble material comprises or consists of iron oxide or titanium dioxide.

7. The method of claim 1, wherein prior to collecting the particles in step (b), a further volume of the first aqueous phase is added to the first dispersion.

8. The method of claim 1, wherein step (d) of adding an aqueous suspension containing the washed surfactant-coated water-insoluble material particles to a polymer solution containing the water-insoluble polymer of the capsule comprises adding dropwise the aqueous suspension containing the washed surfactant-coated water-insoluble material particles to the polymer solution.

9. The method of claim 5, wherein the polymer of the water-insoluble material, the polymer of the further water-insoluble material and the water-insoluble polymer are different.

10. The method of claim 9, wherein the water-insoluble polymer of the capsule has a faster degradation rate than the polymer of the water-insoluble material and the polymer of the further water-insoluble material.

11. The method of claim 1, wherein the polymer of the water-insoluble material is selected from the group consisting of polyanhydride, polyorthoester, polyphosphazene, pseudopolyamino acid, polyamide, polystyrene, ethylene vinyl acetate, polybutadiene, polyurea, (poly)acrylate, methacrylate, acrylate methacrylate copolymer, polyarylsulfone (PAS), polyurethane, polyalkylcyanocarylate, polyphosphazene, polyethylene, fluorinated polyethylene, poly-4-methylpentene, polyacrylonitrile, polyamide-imide, polybenzoxazole, polycarbonate, polycyanoarylether, polyestercarbonate, polyether, polyetheretherketone, polyetherimide, polyetherketone, polyetherimide, polyetherketone, polyethersulfone, polyfluoroolefin, polyimide, polyolefin, polyoxadiazole, polyphenylene oxide, polyphenylene sulfide, polypropylene, polysulfide, polysulphone, polytetrafluoroethylene, polythioether, polytriazole, polyvinyl, polyvinylfluoride, silicone, urea-formaldehyde, poly(e-caprolactone) (PCL), poly(lactic acid) (PLA), poly(L-lactic acid) (PLLA), poly(glycolic acid) (PGA), polyesteramide (PEA), poly(hydroxylbutyrate-co-hydroxyvalerate (PHB or PHBV), polyhydroxyalkanoate, aliphatic copolyester, poly (butylene succinate adipate) (PBSA), aromatic copolyester, poly(butylene adipate-co-terephthalate) (PBAT), poly(L,D-lactic-co-glycolic acid) (PLGA), and copolymers or mixtures thereof.

12. The method of claim 11, wherein the polymer of the water-insoluble material is PLLA.

13. The method of claim 1, wherein the water-insoluble polymer of the capsule is selected from the group consisting of polyanhydride, polyorthoester, polyphosphazene, pseudopolyamino acid, polyamide, polystyrene, ethylene vinyl acetate, polybutadiene, polyurea, (poly)acrylate, methacrylate, acrylatemethacrylate copolymer, poly aryl sulfone (PAS), polyurethane, polyalkylcyanocarylate, polyethylene, fluorinated polyethylene, poly-4-methylpentene, polyacrylonitrile, polyamide-imide, polybenzoxazole, polycarbonate, polycyanoarylether, polyestercarbonate, polyether, polyetheretherketone, polyetherimide, polyetherketone, polyetherimide, polyetherketone, polyethersulfone, polyfluoroolefin, polyimide, polyolefin, polyoxadiazole, polyphenylene oxide, polyphenylene sulfide, polypropylene, polysulfide, polysulphone, polytetrafluoroethylene, polythioether, polytriazole, polyvinyl, polyvinylfluoride, silicone, urea-formaldehyde, poly(s-caprolactone) (PCL), poly(lactic acid) (PLA), poly(L-lactic acid) (PLLA), poly(glycolic acid) (PGA), polyesteramide (PEA), poly(hydroxylbutyrate-co-hydroxyvalerate (PHB or PHBV), polyhydroxyalkanoate, aliphatic copolyester, poly(butylene succinate adipate) (PBSA), aromatic copolyester, poly(butylene adipate-co-terephthalate) (PBAT), poly(L,D-lactic-co-glycolic acid) (PLGA), and copolymers or mixtures thereof.

14. The method of claim 13, wherein the water-insoluble polymer of the capsule is PLGA.

15. The method of claim 1, wherein the first aqueous phase and the second aqueous phase contain the same surfactant.

16. The method of claim 15, wherein the surfactant is selected from the group consisting of sodium dodecyl sulfate (SDS), sodium pentane sulfonate, dehydrocholic acid, glycolithocholic acid ethyl ester, ammonium lauryl sulfate and other alkyl sulfate salts, sodium laureth sulfate, alkyl benzene sulfonate, soaps, fatty acid salts, poloaxamers, alkyl polyethylene oxide), diethylene glycol monohexyl ether, polyvinyl alcohol (PVA), copolymers of poly(ethylene oxide) and polypropylene oxide), hexaethylene glycol monohexadecyl ether, alkyl polyglucosides, digitonin, ethylene glycol monodecyl ether, cocamide MEA, cocamide DEA, cocamide TEA, fatty alcohols, cetyl trimethylammonium bromide (CTAB), dodecylethyldimethylammonium bromide (D12EDMAB), didodecyl ammonium bromide (DMAB), cetylpyridinium chloride (CPC), polyethoxylated tallow amine (POEA), hexadecyltrimethylammonium p-toluenesulfonate, benzalkonium chloride (BAC), benzethonium chloride (BZT), dodecyl betaine, sodium 2,3-dimercaptopropanesulfonate monohydrate, dodecyl dimethylamine oxide, cocamidopropyl betaine, 3-[N,N-dimethyl(3-palmitoylaminopropyl)ammonio]-propanesulfonate, coco ampho glycinate, and mixtures thereof.

17. The method of claim 16, wherein the surfactant is PVA.

18. The method of claim 2, wherein the marker substance is a dye selected from the group consisting of Coumarin-6, Rhodamine 6G, Fluorescein, Umbelliferone, Styryl, Hexacyanin, Dibenzocyanin, Phenoxazon, Pinacyanol, Kryptocyanin, Pyrromethene, Exalite, Quinolon, Stilben, Uranin, Sulforhodamin, and mixtures thereof.

19. The method of claim 2, wherein the therapeutic agent is selected from the group consisting of ibuprofen (IBU), metoclopramide HCl (MCA) lidocaine, atorvastatin, clopidogrel, enoxaparin, celecoxib, omeprazole, esomeprazole, fexofenadine, quetiapine, metoprolol, budesonide, group B *Streptococcus* vaccine (GBS), tetanus toxoid (TT), Japanese encephalitis virus (JEV), diphtheria toxoid (DT), *vibrio cholerae* (VC), SPF 66 malaria vaccine, multivalent vaccines of *Haemophilus* influenza type b (Hib), pertussis toxin (PT), rotavirus, bovine serum albumin (BSA), recombinant human epidermal growth factor (rhEGF), recombinant human erythropoietin (rhEPO), protein-C, ribozymes, vapreotide (somastatin analogue), omtide acetate (LHRH antagonist), growth factors, vascular endothelial growth factor (VEGF), ovalbumin, human chorionic gonadotropin (hCG), human serum albumin (HSA), recombinant human morphogenetic protein-2 (rhBMP), calcitonin, and mixtures thereof.

20. The method of claim 3, wherein the solvent in which the water-insoluble material is dissolved and/or the solvent in which the marker substance and/or the therapeutic agent is dissolved is selected from the group consisting of ethyl acetate (EAc), acetone, methyl ethyl ketone (MEK), tetrahydrofuran (THF), chloroform, pentane, benzene, benzyl alcohol, propylene carbonate (PC), carbon tetrachloride, methylene chloride (dichloromethane or DCM), and acetonitrile.

21. The method of claim 1, wherein the polymer of the water-insoluble material is PLLA and the water-insoluble polymer of the capsule is PLGA.

22. The method of claim 2, wherein the polymer of the water-insoluble material is PLLA and the water-insoluble polymer of the capsule is PLGA.

* * * * *